United States Patent [19]
Leif

[11] 4,348,107
[45] Sep. 7, 1982

[54] ORIFICE INSIDE OPTICAL ELEMENT

[75] Inventor: Robert C. Leif, Coral Gables, Fla.

[73] Assignee: Coulter Electronics, Inc., Hialeah, Fla.

[21] Appl. No.: 170,319

[22] Filed: Jul. 18, 1980

[51] Int. Cl.³ .................... G01N 21/05; G01N 21/64
[52] U.S. Cl. ............................... 356/72; 356/73; 356/246; 356/317
[58] Field of Search .......... 356/72, 73, 246, 410, 356/411, 440, 317, 318, 338; 350/416; 250/222 PC, 576, 458, 459, 461 R, 461 B; 324/71 CP

[56] References Cited

U.S. PATENT DOCUMENTS

| | | | |
|---|---|---|---|
| 2,549,574 | 4/1951 | Condiff | 356/246 |
| 2,707,900 | 5/1955 | Maresh et al. | 356/246 |
| 3,720,470 | 3/1973 | Berkhan | 356/335 |
| 3,972,627 | 8/1976 | Rabl et al. | 356/246 |
| 4,225,229 | 9/1980 | Göhde | 356/39 |

Primary Examiner—Vincent P. McGraw
Attorney, Agent, or Firm—Gerald R. Hibnick

[57] ABSTRACT

Disclosed is an electro-optical transducer for simultaneously making optical measurements and electrical volume measurements on particles suspended in a flow stream passing through an orifice positioned inside an optically clear spherical element.

17 Claims, 6 Drawing Figures

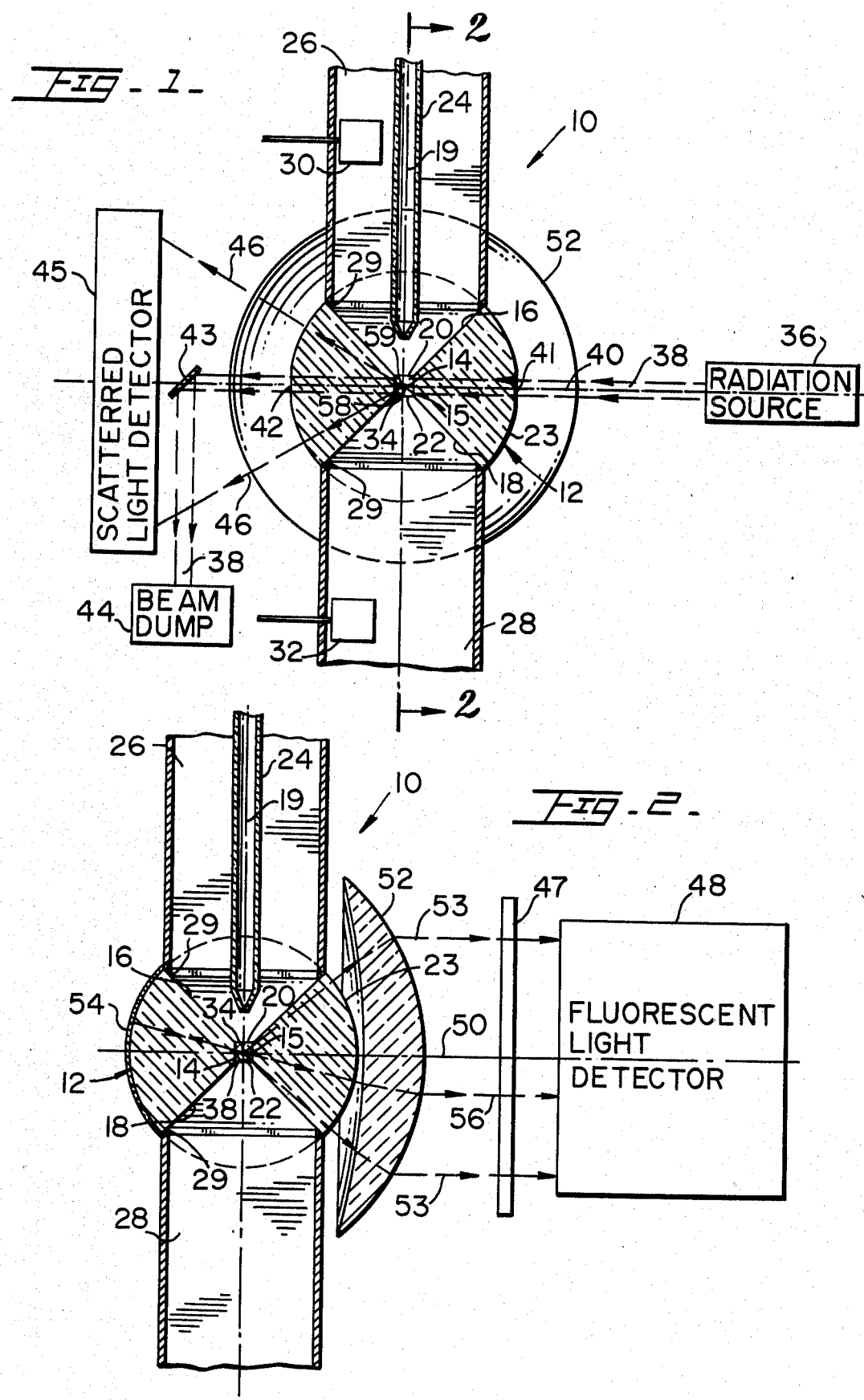

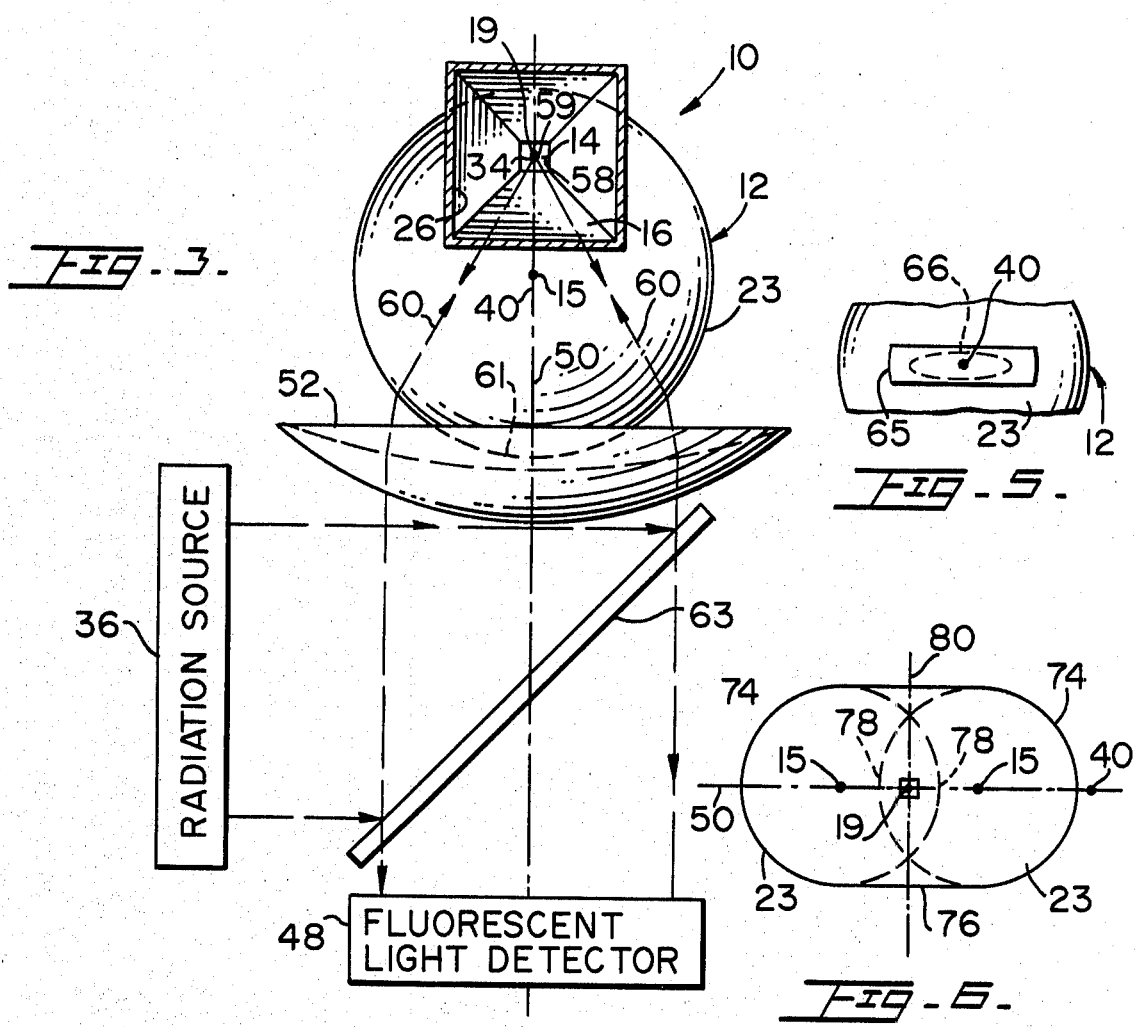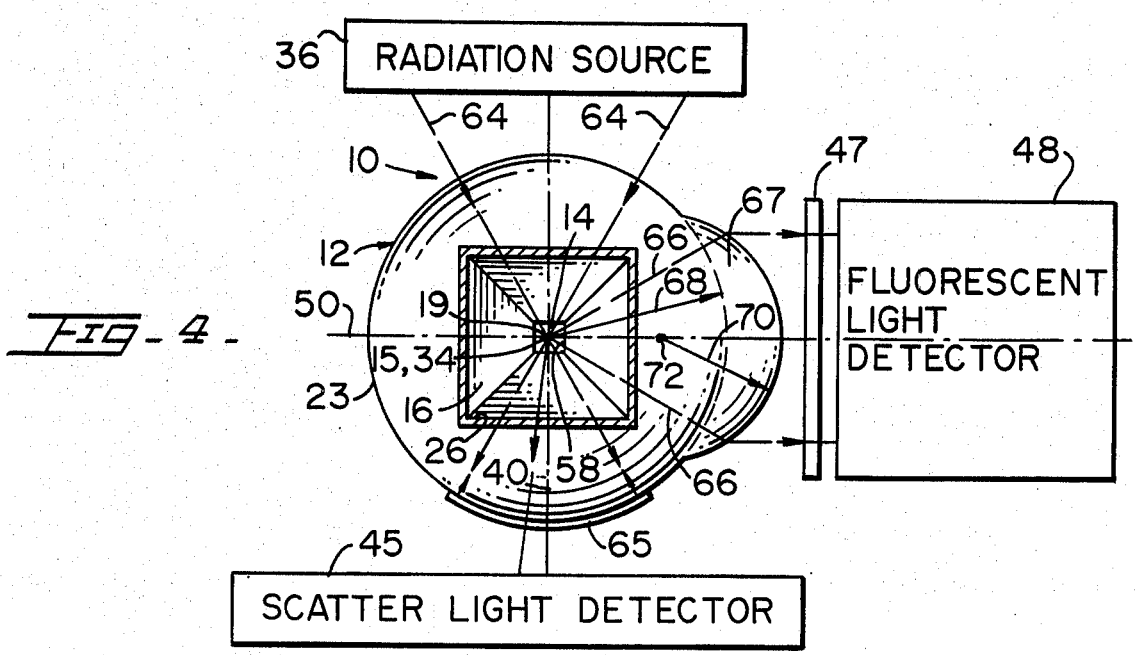

ORIFICE INSIDE OPTICAL ELEMENT

FIELD OF THE INVENTION

The present invention relates to optical flow systems wherein particles in a flow stream are analyzed.

DESCRIPTION OF THE PRIOR ART

For many applications of automated, flow-through particle analyzers, it is not possible to use just a small number of particle descriptors for identification of each type of cell present in a heterodisperse cell population of a sample. At present, most flow systems measure fluorescence, light scattering or electronic cell volume. However, major design problems are brought about by the use of both optical measurements and impedance measurements in a combined electro-optical particle analyzer. Most of the combined electro-optical particle analyzers of the prior art perform electronic cell volume measurements prior to the optical measurements, making it necessary to correlate the two types of measurements. This correlation problem is not significant at very low particle flow rates; however, at high particle flow rates, it is possible for the detected signals to be scrambled by such artifacts as aggregates of cells which pull apart after they traverse a volume-sensing orifice, so as to move separately to the optical sensing zone, the presence of nonfluorescing particles; and the possibility of two neighboring cells exchanging position in the flow stream. The prior art schemes have approached this correlation problem in two ways. One path of development has led to the development of special circuitry for compensating for the time delay between the optical and electronic signals for a given particle. The other path of development has led to an electro-optical particle analyzer in which all measurements are made simultaneously, thereby eliminating the complexity and uncertainty of correlating data obtained from sequential downstream measurements. The latter electro-optical particle analyser is described in an article entitled "Combined Optical and Electronic Analysis of Cells with AMAC Transducers", published in THE JOURNAL OF HISTOCHEMISTRY AND CYTOCHEMISTRY, Vol. 25, No. 7, (1977), pp. 827-835. This multiparameter particle analyzer uses a square sensing chamber or orifice wherein all parameters are measured simultaneously. The square orifice is enclosed inside a cube formed by adhering four pyramids together. However, the optical and mechanical characteristics of this arrangement have proven to be suboptimal.

The collection of diverging fluorescent light, which emanates from a detection zone of the particle analyzer, requires that the light remain fairly organized, so that subsequent optical elements can focus the light for further processing. For instance, to filter stray light out of the fluorescent light, the fluorescent light typically is focused so that it passes through a pinhole aperture. Moreover, barrier filters and photomultiplier tubes work more effectively with light impinging orthogonally on their surfaces. In addition to being organized, the diverging fluorescent light, to be collected, must have a reasonable solid angle with respect to the detection zone. In other words, to focus the light for filtering, or just to create orthogonal light, at least one optical element, such as a collimating lens, is required. The more divergent the light received by the collimating lens, the more power the lens must possess. Practical limitations on an inexpensive collimating lens require that the lens have an f-number no smaller than 0.7, which limits light collection to a half angle of about 40 degrees. The imposition of the optical surfaces of the above described cube causes the light to exit from the flat exterior periphery of the cube in a widely divergent manner. Hence, when using a single, inexpensive conventional collimating lens, only a portion of this widely divergent light can be collected in an organized, collimated beam. For example, when using a square orifice, the amount of light available for precise organization is limited to the area subtended by one of the flat surfaces of the square orifice. When this square orifice is combined with the flat exterior periphery of the cube configuration, not all of the light which impinges upon the flat surface of the orifice can be collected, due to the wide divergence created by the cube configuration. Also, the degree of possible wide angle illumination is greatly curtailed by the cube configuration.

Also, the imposition of the optical surfaces of the cube complicates the collection of scattered light, particularly when the scattered light is correlated with its solid angle of deviation from the center axis of the incident illuminating beam. Also, the optical surfaces of the cube complicate the application of Fourier transform optics.

It is well known in the art of microscopy that the placement of an object within the objective lens results in the greatest light gathering efficiency and resolution. It is also well known that the use of water immersion optics results in greater optical efficiency than dry optics, but not as great an efficiency as that achieved with an immersion medium whose refractive index is equal to that of the lens.

Accordingly, it readily can be seen that there is a need in the art of automated cell analysis for a flow cell wherein the optical characteristics are greatly enhanced over the devices presently existing in the prior art.

The applicant, while developing the hereinafter described invention, was employed and supported by the Papanicolaou Cancer Research Institute of Miami, Florida.

SUMMARY OF THE INVENTION

The invention is directed toward an optically clear flow cell for measuring optical signals generated when particles, which are suspended in a fluid flow stream, pass through an orifice formed in the flow cell and are irradiated by a radiation source. The flow cell has at least one substantially spherical portion for radiation collection. The substantially spherical portion defines a surface of revolution which is radially symmetric with respect to an optical axis, which passes through the orifice. Where a square orifice is used, at least one flat surface thereof is aligned in perpendicular relationship to the light collecting optical axis. In the first embodiment, the flow cell comprises an optically clear spherical element having an orifice disposed at its center. In the second embodiment, the orifice is positioned off-center with respect to the center of curvature of the spherical element.

In operation, the illuminating radiation illuminates individual particles in a flow stream at a detection zone inside the orifice, to produce optical signals; while simultaneously particle impedance measurements optionally can be made on each illuminated particle. In the first embodiment, the detection zone is positioned at the center of the spherical element; hence, the spherical periphery of the spherical element minimizes light refraction of the optical signal, thereby allowing the optical signals to proceed from the spherical element as relatively organized radiation with a reasonable degree of divergence. In the second embodiment, the spherical periphery of the spherical element, along one end of the light collecting optical axis, acts as a more powerful lens so that the radiation proceeds from the spherical element with a relatively small degree of divergence.

The preferred implementation of the first and second embodiments includes the use of an orifice having at least one flat surface. Radiation which emanates from the center of the orifice and impinges upon the flat surface is refracted by a stream-glass interface in a radially symmetric manner about the light collecting optical axis and then is refracted by a glass-air interface of the spherical surface in a radially symmetric manner about the light collecting optical axis, thereby allowing for the efficient collection of highly organized light.

As a variation to the first embodiment of the invention, a portion of the spherical element can have a reflective coating to increase light collection and/or illumination. In both the first and second embodiments, the spherical element can be used with non-collimated illuminating light, instead of collimated light, so as to eliminate problems with uneven illumination within the particles. In both the first and second embodiments, one or more portions of the spherical periphery of the spherical element can be modified to include a spherical portion of greater curvature, to further converge the radiation in an organized manner. In other arrangements, the flow cell has one or more spherical portions and at least one non-spherical portion, to provide additional surfaces for light collection.

BRIEF DESCRIPTION OF THE DRAWINGS

Further objects and advantages of the present invention will become apparent as the following description proceeds, taken in conjunction with the accompanying drawings in which:

FIG. 1 is a cross-sectional side view of the first embodiment of the flow cell of the invention.

FIG. 2 is a cross-sectional side view of the first embodiment of the flow cell of the invention taken along section line 2—2 in FIG. 1.

FIG. 3 is a top plan view of the second embodiment of the flow cell of the invention.

FIG. 4 is a top plan view of a modified first embodiment of FIGS. 1 and 2.

FIG. 5 is a fragmentary view of the modified embodiment of FIG. 4.

FIG. 6 is a cross-sectional top view of a modified second embodiment of FIG. 3.

DESCRIPTION OF THE PREFERRED EMBODIMENTS

Referring to FIG. 1, there is disclosed a first embodiment of an optical flow cell 10 which comprises an optically clear, spherical element 12, preferably formed of quartz. An orifice 14, preferably having a square cross-sectional configuration, is centrally positioned about the center 15 of curvature of the spherical element 12. A pair of opposed connecting passageways, an upstream passageway 16 and a downstream passageway 18, extend outward, respectively, from a pair of open ends 20 and 22 of the square orifice 14, so as to terminate at a spherical periphery 23 of the spherical element 12. Hence, the passageways 16 and 18 and the orifice 14, define a channel for receiving a fluid flow stream through the spherical element 12. The passageways 16 and 18 and the orifice 14 are preferably centered on the flow axis 19 of the flow stream. The passageways 16 and 18 minimize the pressure drop of the flow stream through the spherical element 12.

The well known laminar flow stream technique is preferably utilized, as illustrated in U.S. Pat. No. 3,710,933 to Fulwyler et al. and U.S. Pat. No. 3,989,381 to Fulwyler. A sample introduction tube 24 provides individually isolated particles, such as cells, in a fluid suspension. The introduction tube 24 is surrounded by an upstream chamber 26, which is used to provide a fluid sheath for centering the entrained particles as they pass through the orifice 14. A downstream chamber 28 receives the fluid of the flow stream after it has proceeded through the orifice 14 and the downstream passageway 18. The chambers 26 and 28 are attached in fluid sealed relationship to the spherical element 12 by a pair of conventional seals 29. Although the orifice 14 preferably has a square cross-sectional configuration, it could assume other cross-sectional configurations, for example, a circular configuration. As will be detailed hereinafter, it may be desirable not to have the downstream chamber 28 for certain tranducer implementations, such as cell sorting.

A pair of electrodes, an upstream electrode 30 and a downstream electrode 32, are in electrical communication with both sides of the orifice 14 and have a potential difference applied therebetween. In a manner well known in the art, as illustrated by pioneer U.S. Pat. No. 2,656,508 to Coulter and U.S. Pat. No. 4,014,611 to Simpson et al., impedance sensing of particles flowing through the orifice 14 is accomplished, which provides counting and volume data. The simple arrangement of the two electrodes 30 and 32 is shown only to illustrate one way in which impedance measurements of particles can be accomplished. Other arrangements of electrodes can be used with the flow cell 10, such as those illustrated in U.S. Pat. No. 4,019,134 to Hogg. Hence, a detection zone 34 occurs in the orifice 14, at the center 15 of the spherical element 12 for impedance and counting measurements of entrained particles. Although impedance sensing is shown in the first embodiment, the flow cell 10 can be used solely for the measurement of optical signals to be described hereinafter.

The detection zone 34 is irradiated by a radiation source 36 which provides a relatively collimated beam 38, preferably a laser beam, that is centered on a first optical axis 40. The technique of illuminating a flow stream for detection of absorbed light, fluorescent light and/or scattered light is well known in the art, as illustrated by U.S. Pat. No. 3,710,933 to Fulwyler et al. To incorporate these illuminating techniques, using relatively collimated light into the spherical element 12, a pair of opposed flat surfaces 41 and 42 are formed on the spherical element 12 and are dimensioned and configured to be equal to or greater than the cross-sectional dimensions of the beam 38. Hence, the beam 38 passes through the periphery 23 of the spherical element 12 twice with a minimum of light refraction. That portion of the beam 38 which is not scattered by the entrained particles passes through the spherical element 12, is reflected by a mirror 43, and then is collected in a beam dump 44. The collection of light scattered in a forward direction is accomplished by a forward light scatter detector 45, in a manner disclosed in U.S. Pat. No. 3,710,933 to Fulwyler et al. Moreover, the flow cell 10 does not necessarily require, nor is it limited to the collection of forward scattered light, since the scattered light passing through any of the spherical periphery 23 can be collected and subsequently analyzed in ways well known in the art. In addition, the scattered light can be brought to a focus at a Fourier plane and either detected there on manipulated by well known techniques of optical data processing. An advantage of this first embodiment of the flow cell 10 is that as the scattered light passes through the spherical periphery 23, the spherical element 12 substantially acts as an optical non-element, in comparision to the prior art cube configuration. In other words, the scattered light exits in a substantially perpendicular direction to the spherical periphery 23; hence, the refraction causing wide divergence of the scattered light in the prior art cube is eliminated, as illustrated by light rays 46. However, due to refraction caused by the stream-glass interface, the exiting light will be slightly less divergent with respect to their incident direction in the orifice 14.

FIG. 2 is a cross-sectional view of the flow cell 10 taken with respect to a section plane passing through the center of the spherical element 12 and passing perpendicular to the plane of the drawing of FIG. 1. As is standard practice in the art, fluorescent light emanating from the detection zone 34 preferably is collected at right angles to the beam 38. More specifically, in the first embodiment, a barrier filter 47 and a fluorescent light detector 48 are centered on a second optical axis 50, which preferably is perpendicular to the first optical axis 40. Ideally, the first optical axis 40 and the second optical axis 50 define a plane which substantially is perpendicular to the flow axis 19 of the flow stream. In order to provide collimated light to the barrier filter 47 and the detector 48, a collecting lens 52 is used. Ideally, the collecting lens 52 is positioned immediately adjacent to the spherical element 12. Arrangements of lenses and detectors are well known in the art, as illustrated by U.S. Pat. No. 3,710,933 to Fulwyler et al. As with the scattered light, the fluorescent light intersects the spherical periphery 23 with a substantially orthogonal approach, hence, refraction of the fluorescent light is minimized. As illustrated by light rays 53, the spherical periphery 23 allows for the fluorescent light to leave the spherical element 12 in an organized manner with a minimum of refraction. Hence, the wide angle divergence caused by the cube configuration of the prior art is eliminated. In fact, the small amount of refraction introduced by the first embodiment slightly decreases the divergence of the exiting light.

An optional feature for the first embodiment of the flow cell 10, as shown in FIG. 2, is a reflective coating 54 applied to one side of the spherical periphery 23. As shown by the illustrative light ray 56, a portion of the light emanating from the detection zone 34 reflects from the reflective coating 54, then proceeds through the detection zone 34 and subsequently is collected. Numerous variations to the collection of fluorescent light or any other optical signal will be obvious to those skilled in the art. For instance, the reflective coating 54 can be made of a dichroic material so as to reflect one wavelength range of radiation, but allow another wavelength range to pass through. Additionally, another wavelength of fluorescent light or scattered light could be collected on the side of the spherical element 12 shown in FIG. 2 to have the reflective coating 54. Such additional collection could be accomplished by excluding the reflective coating 54 or including a known type of dichroic reflective coating 54 capable of separating fluorescent light of different wavelengths. It will be appreciated by those skilled in the art that the flow cell 10 can be used for the collection of fluorescent light only or scattered light only or, as in the first embodiment, some combination thereof. Moreover, the flow cell 10 can be used with well known slit scanning techniques and for fluorescent light polarization studies. For example, in polarization studies, linearly polarized light of a laser impinges upon the particles and is partially depolarized. The fluorescent intensities polarized parallel and perpendicular to the plane of the polarized incident light are measured. Such measurements require that the fluorescent light signals remain optically organized. Hence, the flow cell 10 can be used to collect any optical signal which proceeds from the detection zone 34.

Another advantage of the spherical element 12 is that a non-collimated illumination can be supplied by the source 36 in place of the collimated beam 38. More specifically, the radiation source 36 could provide a beam which is convergent on the detection zone 34. Hence, the incident light orthogonally impinges upon the spherical pheriphery 23, thereby minimizing light refraction, to allow the light to come to a focus at the detection zone 34. Non-laser light sources, such as mercury or xenon arc lamps and conventional episcopic microscopic illumination, can be used instead of laser illumination with the flow cell 10. However, non-collimated light sources curtail the measurement of forward light scatter.

The downstream chamber 28 can take many different forms well known in the art. It can be a simple chamber used for the disposal of the liquid from the flow stream, such as shown in U.S. Pat. Nos. 3,746,976 to Hogg and 4,014,611 to Simpson et al. Alternatively, the formation of droplets (not shown) with individually isolated particles therein, with subsequent droplet sorting, can be incorporated into the flow system of the flow cell 10. In this case, the downstream chamber 28 would not be needed and the downstream passageway 18 would be in direct communication with the surrounding atmosphere. One way to do this would be to use a grounded second sheath arrangement as shown in U.S. Pat. No. 3,710,933 to Fulwyler et al. or, alternatively, use a grounded plate arrangement as shown in U.S. Pat. No. 3,380,584 to Fulwyler. If the sorting feature is incorporated, it is desirable for the orifice 14 to have a depth to width ratio of approximately 4 to 1. Without sorting, it is desirable for this ratio to be approximately 1 to 1. The width of the orifice 14 can vary, depending on the size of the particles to be analyzed. Although the spherical element 12 is formed preferably of quartz, other materials which are highly light transmissive, with a low refractive index, such as plastic or sapphire, can be used in specific applications.

Heretofore, the first embodiment of FIGS. 1 and 2 has been described as being used for the study of particles, such as biological cells, which are introduced by means of the sample introduction tube 24. Another implementation of the transducer 10 is in the art of chromatography, wherein optical flow cells commonly are used to analyze a fluid chromatographic effluent. In the chromatographic art area, the previously described laminar flow techniques, and therefore the sample introduction tube 24, may or may not be used. Consequently, the species to be detected may or may not be centered in the liquid or glass flow stream. The term "particle" is defined herein to include the fluorescing molecules of the fluid chromatographic effluent.

Referring to FIGS. 1 and 2, the square orifice 14 is shown with flat surfaces 58. As is known in the art, light emanating from a center 59 of the orifice 14 intersects each flat surface 58 such that the refraction introduced by the stream-glass interface of the flat surface 58 bends the light in a radially symmetric manner about the optical axes 40 and 50. Any further refraction caused by the spherical periphery 23 will likewise cause radially symmetric bending about the optical axes 40 and 50. Hence, the unique combination of the spherical periphery 23 and at least one of the flat surfaces 58 allows for light to be collected along the optical axis 50, with the resulting refraction causing radially symmetric light bending. This means that inexpensive spherical lenses, such as the collecting lens 52, can be used to collect the light in a highly organized beam. Although not shown, the fluorescent detector 48 could be also positioned on the second optical axis 40 and utilize the above described advantages of the flat surfaces 58. However, the radiation source 36 and its associated optical elements will interfere, to a limited degree, with light collection. Also, the stream of particles can be positioned off-center with respect to the center of the square orifice 14, so that one of the flat surfaces 58 subtends a greater area with respect to the particles. Hence, this allows for a wide angle of light collection and square shaped pulses for impedance sensing.

Referring to FIG. 3, there is illustrated a second embodiment of the flow cell 10 wherein the flow axis 19 of the orifice 14 is positioned off-center with respect to the center 15 of the spherical element 12. As is known in the microscope art, the off-center positioning of a light source in a spherical lens element can produce a lens element having a numerical aperture as large as 1.4. More specifically, radiation proceeding from the orifice 14 intersects the spherical periphery 23 so as to be refracted in a radially symmetrical manner with respect to the second optical axis 50. Consequently, light rays 60, which proceed from the orifice 14 to a remotely disposed portion 61 of the spherical element 12, are refracted inward toward the second optical axis 50. By virtue of this inward bending, a less divergent beam, centered on the optical axis 50, proceeds from the spherical element 12 and is collimated by the collecting lens 52. However, as compared to the collecting lens 52 of the first embodiment, the collecting lens 52 of the second embodiment requires much less power for the same light collection; hence, substantial cost savings. Alternatively, a collecting lens 52 of the same power can be used to intercept and collimate substantially more light. More specifically, nearly all of the light proceeding from one of the flat surfaces 58 of the square orifice 14 can be collected by the collecting lens 52 into a collimated beam. The radiation source 36 provides convergent illumination, as shown by the two directional illustration of the light rays 60. This is accomplished by the use of a conventional dichroic mirror 63, which can be used to reflect illuminating radiation, while passing through fluorescent light or vice versa. The lens 52 is used to converge the illuminating light, and to collimate the exiting fluorescent light. The lens 52 can be either spaced apart or attached to the spherical element 12. In the first embodiment of FIGS. 1 and 2, organized light could be collected, even though the optical axes 40 and 50 are not perpendicular to the flow stream axis 19. However, in the second embodiment as shown in FIG. 3, the optical axes 40 and 50, which are colinear, must be perpendicular to the flow stream axis 19. Also, the second optical axis 50 must pass substantially through the center 15 of the spherical element 12. Moreover, if wide angle illumination is desired, the first optical axis 40 must be colinear with the second optical axis 50. In other respects, the construction and operation of the second embodiment are the same as the first embodiment.

FIG. 4 illustrates two modifications to the heretofore described embodiments. The radiation source 36 provides radiation which is convergent in the plane of the drawing as illustrated by light rays 64. In a direction perpendicular to the drawing, the radiation provided by the radiation source 36 is relatively narrow and slightly convergent. Hence, the light rays 64, in a converging, "slit-like" beam, are directed toward the orifice 14. Since such rays are substantially perpendicular to the spherical periphery 23, a minimum amount of refraction of the exiting radiation is caused by the air-glass interface of the spherical surface. Although a minute amount of deviation is caused by the glass-stream interface of the orifice 14, the converging radiation will illuminate the particles proceeding through the orifice 14. A small band of a reflective coating 65 is applied to the spherical periphery 23 to define a reflective mirror for intercepting the illuminating radiation after it passes through the orifice 14. The reflective coating 65 is illustrated in detail in FIG. 5, with the configuration of the illuminating radiation, as it impinges upon the reflective coating 65, being illustrated by the substantially elliptical configuration 66. The width of the reflective coating 65 is minimized with respect to the illuminating radiation, so that light scatter can be detected above and below the reflective coating, by use of the scatter light detector 45. It is possible to place the flow cell 10 in a laser cavity, with the reflecting mirror. This arrangement allows for the use of an inexpensive, less powerful light source. Additionally, wide angle illumination of the particles, as is known in the art, decreases problems normally encountered by illuminating biological cells with relatively narrow beams. More specifically, illumination of cells with relatively narrow beams of illuminating radiation, such as laser light, creates "hot spots", i.e., regions of relatively large energy density as compared to neighboring regions within the cell. In other words, regions of nonuniform radiation or "hot spots" represent uneven illumination, so that all parts of a cell are not exposed to the same amount of energy. These "hot spots" are due to the optical effects at cell and organelle boundaries. This is particularily true of cells being irradiated by collimated radiation. Moreover, it is known in the art that converging beams, e.g., laser radiation, with a Gaussian intensity profile, become collimated in the focal region due to diffraction and therefore create the "hot spots" in the same manner. The problem with these "hot spots" is that if they coincide in location with the regions of fluorescent material within the cell, then that fluorescent material gives off a high intensity fluorescent signal relative to a low intensity fluorescent signal that the same fluorescent material would have produced if it had not been in the "hot spot". In short, if the "hot spot" is coincident with the fluorescent material, an inaccurate fluorescent reading is obtained. Wide angle illumination, such as that shown in FIGS. 3 and 4, minimizes the above described problems. Also, cells trap light so that light does not emanate from the cells uniformly.

Referring to FIG. 4, a region of the spherical pheriphery 23 is modified to include a protruding, spherical lens portion 67 having a greater curvature than the spherical periphery 23, so that collimated light can be achieved without the inclusion of separate optical elements, such as the collecting lens 52. These lens portions can be integrally formed on the spherical element 12 or they can be separate pieces that are attached to the spherical element 12. The spherical element 12, is, by itself, a monolithic element. The monolithic nature of spherical element 12 gives improved light collection by the elimination of adhered surfaces. More specifically, the glue used in the adhered surfaces causes optical inhomogeneities, which produce stray light. The inhomogeneities can fluoresce and with time the glue can fall apart. As illustrated in FIG. 4, the spherical periphery 23 is defined as having an outer radius 68, which is equal to the inner radius of the spherical lens portion 67. The spherical lens portion 67 has an outer radius 70 which rotates about a center of curvature 72 positioned on the second optical axis 50. The outer radius 70 is dimensionally smaller than the radius 68; hence, the exterior curvature of the lens portion 67 is greater than that of the spherical periphery 23. Clearly, the scope of the present invention includes not only the spherical element 12, but can include one or more spherical portions, such as lens portion 67, or can include one or more aspherical portions integrally formed on the spherical element 12 or attached thereto.

With respect to FIG. 6, it will be evident to those skilled in the art, that the spherical element 12 can be formed into an optical element having one or more spherical portions, such as a pair of opposed spherical portions 74, and one or more nonspherical portions, such as a cylindrical portion 76. The embodiment illustrates how spherical portions, shown by spherical outlines 78 and spherical peripheries 23, can be joined so that the off-center relationship of the orifice 14 can be used to collect light from multiple spherical portions 74. In addition, more than two spherical portions 74 can be joined about the orifice 14. Wide angle illumination of the orifice 14 can be used, for example, by providing convergent radiation centered on the first optical axis 40, with the second optical axis 50 for collection being colinear therewith. Alternatively, for example, convergent, "slit-like" illumination can be provided along an optical axis 80, with the cylindrical portion 76 acting like a converging lens to the wide dimensions of the cross section of the "slit-like" beam.

Referring to the drawings in general, all embodiments of the flow cell 10 define an optical element having at least one or more spherical portions that are radially symmetric with respect to a selected position of the second optical axis 50. In the first embodiment of FIGS. 1 and 2, as long as the second optical axis 50 passes through the center 15, the second optical axis 50 can assume any position, with the entire spherical periphery 23 defining an opposed pair of spherical portions. In the second embodiment of FIG. 3, the second optical axis 50 must pass through the orifice 14 and the center 15, which are now spaced apart, so that the remotely disposed portion 61 defines a spherical portion which is radially symmetric about the second optical axis 50. In the modified embodiment of FIG. 4, both the spherical periphery 23 and the spherical lens portion 67 are radially symmetric with respect to the second optical axis 50, with both centers of curvature 15 and 72 being positioned thereon. In FIG. 6, both of the pair of centers 15 and the orifice 14 are positioned on the second optical axis 50. If a square orifice 14 is used, at least one of its flat surfaces 58 will be orientated to be perpendicular to the second optical axis 50.

Referring to the drawings in general, any of the spherical portions, such as spherical periphery 23, spherical lens portion 67, or spherical portions 74 can be made aspherical to, for example, correct for spherical aberration. Hence, these surfaces will be referred to in the claims as being "substantially spherical portions" or as "peripheral convex portions defining a surface of revolution". More specifically, the surface of revolution comprises an appropriate curved line revolved about an optical axis to generate a radially symmetric surface. For simplicity, such aspherical portions will be assumed to have centers of curvature of the spherical configurations most closely corresponding to the aspherical portions.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle analyzing apparatus for studying individual microscopic sized particles in liquid suspension, said apparatus including a flow cell having a particle sensing orifice through which a stream of said particles in suspension are passed, radiation source means for providing radiation to illuminate a given particle in said particle sensing orifice, radiation detector means responsive to optical signals caused by the passage of said given particle through said radiation for generating an analog electrical signal, said flow cell having an upstream passageway and a downstream passageway formed in opposed ends of said flow cell, said particle sensing orifice being disposed in liquid connecting relationship between said passageways, the improvement being characterized by:

said flow cell comprising a substantially spherical element;

said spherical element having a monolithic structure;

a light illumination optical axis along which said radiation is provided by said radiation source means and at least one light collecting optical axis along which said optical signals are collected by said radiation detector means, said optical axes being aligned to intersect said orifice, and said spherical element being essentially radially symmetric with respect to said optical axes.

2. The particle analyzing apparatus according to claim 1 wherein said orifice includes at least one flat surface, said flat surface being disposed in perpendicular relationship to said light collecting optical axis.

3. The particle analyzing apparatus according to claim 1 wherein said orifice is disposed in surrounding relationship to the center of curvature of said spherical element.

4. The particle analyzing apparatus according to claim 1 wherein the center of curvature of said spherical element is positioned between said orifice and said spherical element.

5. The particle analyzing apparatus according to claim 1 wherein at least one peripheral region of said spherical element has a curved lens portion extending beyond the outer radius of the spherical element, said curved lens portion being positioned on said light collecting optical axis.

6. The particle analyzing apparatus according to claim 5 wherein said curved lens portion is defined by an inner radius and an outer radius, said inner radius being equal to the outer radius of the spherical element, said outer radius of said curved lens portion being smaller than said inner radius.

7. The particle analyzing apparatus according to claim 1 wherein said spherical element has a pair of opposed flat surfaces formed therein, said flat surfaces being positioned on said optical illumination axis for illumination, said illumination optical axis being disposed in perpendicular relationship with said flat surfaces and wherein said radiation source means is operative to provide collimated radiation centered on said illumination optical axis.

8. The particle analyzing apparatus according to claim 1 wherein said radiation source means is operative to provide convergent radiation substantially focused on said orifice.

9. The particle analyzing apparatus according to claim 1 wherein the orifice is positioned in surrounding relationship to the center of curvature of said spherical element and further including,
a portion of said spherical element having a reflective coating, said coated portion of said spherical element being positioned on said light collecting optical axis and on the side of said spherical element opposite to said radiation detector.

10. The particle analyzing apparatus according to claim 1 wherein said orifice is positioned in surrounding relationship to the center of curvature of said spherical element and wherein said radiation source means is operative to provide convergent radiation, having a slit-like cross-sectional configuration, which is substantially focused on the orifice and further including,
a narrow band of reflective coating mounted on said spherical element to reflect said convergent radiation after it passes through said orifice.

11. The particle analyzing apparatus according to claim 1 wherein the center of curvature of said spherical element is positioned between said orifice and the periphery of said spherical element, said optical axis and illuminating axes are disposed in coincident relationship, and further including,
a dichroic mirror positioned on said optical axes, whereby said dichroic mirror allows for both light collection and irradiation along the same axis.

12. The particle analyzing apparatus according to claim 4, wherein the flow cell has an opposed pair of overlapping said spherical elements which are radially symmetric with respect to said light collecting axis, said pair of spherical elements having their centers of curvature spaced apart with respect to each other, said orifice being positioned between the centers of curvature.

13. The particle analyzing apparatus according to claim 12 wherein a cylindrical portion is interposed in joining relationship between said pair of spherical portions.

14. The particle analyzing apparatus according to claim 1 further including,
a pair of chambers, each said chamber being mounted essentially at the extremity of one of said passageways adjacent the periphery of said flow cell.

15. The particle analyzing apparatus according to claim 1 further including,
a collecting lens being interposed between said flow cell and said radiation detector means.

16. The particle analyzing apparatus according to claim 1, further including,
means for passing an electric current through said orifice simultaneously with passage of a particle through said orifice; and
detecting means responsive to electrical impedance variations for generating a particle pulse signal with the passage of said particle through said orifice.

17. The particle analyzing apparatus according to claim 1, wherein said flow cell further comprises a plurality of light collecting optical axes for collecting radiation; each said light collecting optical axes being disposed to intersect said orifice; a plurality of radiation detector means are positioned on each said light collecting optical axis for collecting said optical signals.

* * * * *